United States Patent
Bley

(10) Patent No.: US 6,708,882 B1
(45) Date of Patent: Mar. 23, 2004

(54) METHOD AND SYSTEM FOR REPRESENTING CHEMICAL STRUCTURAL FORMULAE

(75) Inventor: Klemens Bley, Darmstadt (DE)

(73) Assignee: Merck KGaA, Darmstadt (DE)

( * ) Notice: Subject to any disclaimer, the term of this patent is extended or adjusted under 35 U.S.C. 154(b) by 11 days.

(21) Appl. No.: 10/009,769

(22) PCT Filed: Jun. 16, 2000

(86) PCT No.: PCT/EP00/05554

§ 371 (c)(1), (2), (4) Date: Dec. 17, 2001

(87) PCT Pub. No.: WO00/79358

PCT Pub. Date: Dec. 28, 2000

(30) Foreign Application Priority Data

Jun. 22, 1999 (DE) ........................................ 199 28 512

(51) Int. Cl.⁷ ................................................. G06K 7/10
(52) U.S. Cl. .................... 235/462.01; 703/12; 707/266; 707/268; 705/2
(58) Field of Search ................................. 235/383, 385, 235/462.01; 705/28, 2; 707/3; 700/266, 268; 702/22, 27; 260/1; 422/187; 703/12

(56) References Cited

U.S. PATENT DOCUMENTS

| | | | | |
|---|---|---|---|---|
| 5,577,239 A | * | 11/1996 | Moore et al. .................. | 707/3 |
| 5,612,894 A | * | 3/1997 | Wertz .......................... | 702/27 |
| 5,845,264 A | * | 12/1998 | Nellhaus ...................... | 705/28 |
| 5,880,972 A | * | 3/1999 | Horlbeck ...................... | 702/27 |
| 5,950,192 A | * | 9/1999 | Moore et al. .................. | 707/3 |
| 6,061,636 A | * | 5/2000 | Horlbeck ...................... | 702/22 |
| 6,088,629 A | * | 7/2000 | Tomonaga et al. ........... | 700/266 |
| 6,155,485 A | * | 12/2000 | Coughlin et al. ............ | 235/383 |
| 6,311,134 B1 | * | 10/2001 | Sorenson ..................... | 702/22 |
| 6,377,895 B1 | * | 4/2002 | Horlbeck ...................... | 702/22 |
| 6,600,970 B2 | * | 7/2003 | Bley .......................... | 700/268 |

FOREIGN PATENT DOCUMENTS

DE   4115355 A   11/1992
EP   0863467 A   9/1998
JP   2002207826 A  *  7/2002  ........... G06F/17/60

OTHER PUBLICATIONS

STN International c/o Chemical Abstract Service "Seminar Materials," Jul. 1, 1997, pp. 45–50.

Synopsis White Paper : Acord Combichem Tools, 'Online! 1998, Retrieved fron the Internet: <URL :www.synopsys.co.uk> Retrieved on Jan. 15, 2001.

* cited by examiner

Primary Examiner—Michael G. Lee
Assistant Examiner—Daniel I Walsh
(74) Attorney, Agent, or Firm—Millen, White, Zelano & Branigan, P.C.

(57) ABSTRACT

The present invention concerns a method of representing chemical structural formulae on a display device by means of a chemical symbol or graphic program for producing chemical structural formulae, and a system for representing chemical structural formulae having an apparatus for carrying out the method according to one of claims 1 to 3, comprising a computer and a symbol or graphic program installable thereon for representing chemical structural formulae and at least one memory. In order to provide a method and a corresponding system for representing chemical structural formulae on a display device, by means of which the preparation of chemical reaction equations on the basis of structural formulae is substantially simplified, it is proposed in accordance with the invention that codings are allocated to known or newly synthesised chemical substances, that the codings are stored in a memory which can be connected to the symbol program, wherein in relation to each code of a chemical substance the associated structure or a program routine for production of the structure are also stored, and that the code is applied in a readable or machine-readable form to an article with unequivocal association with the substance so that from there it can be inputted into a computer on which the symbol program is running, wherein by virtue of the input of the code the representation of the corresponding structure on the display device can be triggered.

6 Claims, No Drawings

METHOD AND SYSTEM FOR REPRESENTING CHEMICAL STRUCTURAL FORMULAE

The present invention concerns a method of representing chemical structural formulae on a display device by means of a chemical symbol or graphic program for producing chemical structural formulae.

Corresponding symbol programs have already long been known. Symbols programs of that kind generally have a set of basic structural elements of chemical structural formulae, wherein each of those structural elements can be moved to or produced at a desired position on a display screen. In that situation the area of a corresponding display device which can be for example a display screen or a printed surface is generally divided into equal surface elements and at least one structural element, for example a line of a single bond or a double line for a double bond is associated in a given spatial orientation in each surface element. The structural elements are also generally rotatable and/or displaceable within the surface element so that structural elements of adjacent surface elements can always be suitably fitted together. The individual surface elements can possibly also be rotatable in their entirety.

The basic structural elements for corresponding symbol programs which are used almost exclusively in the area of organic chemistry are therefore single, double or triple bonds in the form of a single, double or triple line, the ends of which respectively define the position of the ions or atoms which are connected in that way. In that respect a plurality of corresponding lines may also be joined together at predetermined angles or also with short interruptions, but in that case corresponding symbol programs are generally restricted to affording a few basic structures in the form of complex structural elements, for example a so-called benzene ring, that is to say the structure of a regular hexagon with alternate double and single bonds. Admittedly, any chemical structures can be composed therefrom by the addition of further bonding lines, but such more complex structures are generally not available from the outset as fundamental structural elements.

In that respect, in accordance with a normal convention, the carbon atoms which are possibly present at the ends of the bonds or bonding lines are not expressly identified, in other words, where two lines, without being identified in greater detail, meet with a short interruption or at an angle <180°, there is a respective carbon atom. If however other elements such as nitrogen, hydrogen, oxygen or sulphur or also molecules form the termination of a bonding line, then the ends of such lines are identified with suitable letter identifications, corresponding to the usual chemical nomenclature.

In the synthesis of new chemical compounds in chemical research and development but in part also in the analysis of given substances, corresponding chemical structural formulae are an essential aid for the chemist as he can recognise which parts of a chemical structure are in any way available for a reaction with other substances or components, by reference to the structural formula, substantially better than by reference to a corresponding sum formula or a chemical identification, even if it is a precise one. In that way desired compounds or structures can be synthesised substantially more easily and in a more specific and targeted fashion and existing structures are identified substantially more easily on the basis of their fragments or also on the basis of their reaction behaviour.

In that respect the procedure in chemical research is generally such that structural formulae are noted for starting substances (educts) and a product which possibly results therefrom. As corresponding research results must also be archived and documented, in regard to the presentday demands on documentation and accessibility and searchability of corresponding results, it is necessary for the corresponding reaction equations to be electronically stored if possible with the structural formulae. It will be appreciated that the symbol or graphic programs which already exist for producing chemical structural formulae are in principle the appropriate instrument.

However the preparation of corresponding reaction equations or the individual educts and products on the display screen is a procedure which is often expensive, tedious and involved if the structures of the chemical educts and products are correspondingly extensive and complicated. More specifically, in that case very many individual basic elements which the chemical symbol program offers are put together piece by piece. That requires a relatively great amount of time and also entails a serious source of error as it is certainly possible for individual structural elements, by mistake, to be omitted, added or inserted at a wrong position or in a wrong orientation.

In comparison with that state of the art the object of the present invention is to provide a method and a corresponding system for representing chemical structural formulae on a display device, by means of which the preparation of chemical reaction equations, on the basis of structural formulae, is substantially simplified.

In regard to the method that object is attained in that codings are allocated to known or newly synthesised chemical substances, that the codings are stored in a memory which can connect to the symbol program, wherein in relation to each code of a chemical substance the associated structure or a program routine for production of the structure are also stored, and that the code is applied in a readable or machine-readable form to an article with unequivocal association with the substance so that from there it can be inputted into a computer on which the symbol program is running, wherein by virtue of the input of the code the representation of the corresponding structure on the display device can be triggered.

In the case of this method therefore the chemist himself does not have to compose the structural formula of a chemical substance as a laborious piece of detailed work on the basis of a chemical identification and a sum formula, but he merely inputs a code associated with the substance into a suitable computer, in which case then, by virtue of the symbol program, the complete structure of that substance is either called up from a memory or produced by a program routine associated with the code.

It will be appreciated that the code must be present in some readable form so that it can be inputted into the computer, in which respect the term 'readable' is used to mean both codings which are readable by people and also machine-readable, such as for example the known bar codes, or also a coded storage in magnetic form on a magnetic strip or also on corresponding optical storage devices. Machine plain text readers which can correctly read digits printed on a surface would certainly also be considered. Input of the code can also be again considerably simplified by the use of a suitable reading device, so that within fractions of a second the desired structure for example appears on a display screen, can be printed out or is made available in some other manner for representation.

In that respect it will be appreciated that it is desirable if the code is applied to a container of a chemical substance, to a label relating thereto, an instruction leaflet or list of contents, or a table work. It would therefore be desirable if in a chemical laboratory any container in which a chemical substance is stored which is involved as an educt of a chemical reaction is provided with a suitable coding printed thereon. In that respect for example it is possible for article numbers which are already present in any case and which unequivocally identify a chemical substance to be used as codings. As already mentioned bar codes can also be printed on a container or a label applied to the container. If necessary however it is also possible to provide a table work which, besides a normal chemical identification of a substance, also specifies a corresponding coding, for example in the form of a bar code, so that it is only necessary to pass a reading pen or the like of a bar code reader over that stored bar code beside a substance specified in the usual chemical nomenclature in order to implement the desired input into a computer, whereupon the structure in question appears for example on a display screen.

In the case of mixtures, solutions, emulsions or mixes of substances which do not chemically react with each other but which in fact can respectively react with another (common) educt, the structure of the individual components is desirably reproduced with a '+' symbol therebetween solely on the basis of the corresponding coding for the mixture, solution, emulsion or mix of substances, on the display device.

If a plurality of educts which are stored separately (in containers) and which react with each other to form one or more new products are otherwise brought together, then the various codings of the educts can be successively inputted so that they successively appear in a row on a display screen or the like and are possibly connected by plus symbols. If the final products can already be read off from the starting products or educts and differ for example only in respect of details from one of the educts, it is desirable for that educt to be represented once again on the right-hand side of a chemical reaction equation and to implement only the required modifications. It is assumed in that respect that the resulting product is novel and that there is not yet any coding for that new structure so that then a corresponding new code number has to be allocated for the new substance. If however the product should already be known per se, it would optionally also be possible to call up the associated coding from a table in order thereby still further to simplify representation.

A corresponding system having an apparatus for carrying out such a method, which comprises a computer and a symbol or graphic program which is or can be installed thereon, for representing chemical structural formulae, and which also has a suitable memory, to attain the above-specified object, is characterised in that the memory is designed for the storage of codes and that in addition there is provided storage space for chemical structures associated with the codes or for program routines producing the representation of said structures, wherein there are provided input devices for input of the codes and the codes are held in readiness in a readable form and in unequivocal association with the associated chemical substances.

The input devices in the simplest case comprise a keyboard by way of which only the coding needs to be inputted, or still more preferably a mouse, by means of which the desired chemical structural formula can be produced for example by selection (clicking on) in an electronically stored table work. The input device however may also be a plain text reader, a bar code reader or another optical or magnetic reading head, depending on the respective form in which the codes are stored. In that respect, it is only necessary to note that the codes are unequivocally associated with given chemical substances, which, as already mentioned, is most easily effected by the codes being printed on containers which contain the associated chemical substance.

Further advantages, features and possible uses of the present invention will be clearly apparent from the description hereinafter of a preferred embodiment and the associated Figures.

By way of example, a reaction equation in which acetanilide results from the reaction of aniline with acetyl chloride is to be represented in the form of structural formulae.

In this respect, for the purposes of the present description, it will be assumed that codes corresponding to aniline and acetyl chloride have already been allocated to the two educts and stored, whereas acetanilide is to assume the part of a new, as yet unknown substance, the formation of which however can be clearly easily understood by reference to the chemical structural formulae of the educts.

In this case for example the code of the aniline is inputted by way of a bar code reader from an aniline bottle, on the label or the outside of which a suitable bar code is printed or embossed. In that case the following structure appears, wherein the arrow which separates the right-hand side of a reaction equation from the left-hand side is produced automatically:

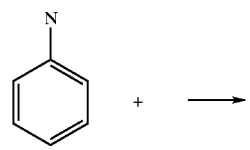

As acetanilide differs in terms of chemical structure from aniline only at a few locations, it is desirable, for representation on the right-hand side of the reaction equation, to again call up the code for aniline so that, starting from that structure, it is only necessary to implement the modifications which make therefrom the above-mentioned acetanilide. That intermediate stage is illustrated in the equation hereinafter by means of the corresponding structural formulae.

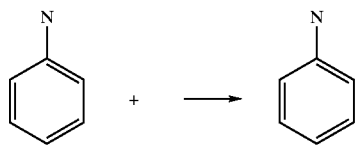

Then, on the left-hand side, beside a '+' symbol, the code of acetyl chloride is also called up and the structure illustrated there, so that firstly the image which occurs is as follows:

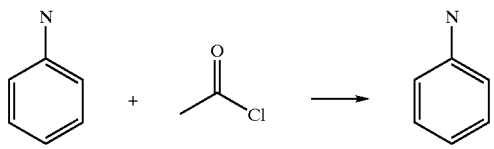

Now the necessary additions also have to be effected on the right-hand side. For this purpose also firstly the structure of acetyl chloride can be fitted as an appendage to the already existing aniline structure and final correction is then effected merely by removal of the letters Cl for chlorine from that structure and input of the additional product ClH, in which respect the detailing of by-products which are not of interest can also be omitted.

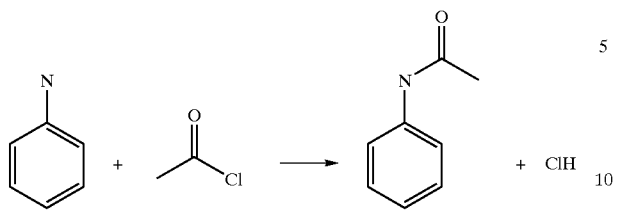

It will be appreciated that the foregoing example is an extremely simple example in which the saving in time, in relation to constructing the individual structures within a normal chemical symbol program, is not yet very clearly apparent. The educts however can also be substantially more complicated and can be composed of a large number of benzene rings, chains and other structures, so that, upon calling up a code number for a substance which is more complicated in accordance with its chemical structure, this represents a considerable simplification. It will be appreciated that the sequence of steps set forth in the foregoing example can be altered, for example in such a way that the reaction equation is constructed step by step from left to right.

In that respect moreover it is desirable if the system is so designed that basically all already known chemical substances and also new synthesised chemical substances are stored as quickly as possible in a central database, with their corresponding structural formulae and an associated code, in which case a local computer then only has to have a suitable connection to the database, but the data themselves can be managed elsewhere.

Even without further information it is assumed that a man skilled in the art can use the foregoing description to the broadest extent. The preferred embodiments and examples are accordingly to be viewed only as a descriptive disclosure which is in no way to have a limiting effect in any fashion.

The complete disclosure of corresponding application No. 199 28 512.8 filed on Jun. 22nd 1999 is incorporated into this application by reference thereto.

What is claimed is:

1. A method of representing chemical structural formulae of compounds and of their reaction product or products on a display device by a chemical symbol or graphic program for producing chemical structural formulae, comprising a) preparing a database or using one or more preexisting databases on a computer that stores
a set of codes, each code being allocated to a compound or composition containing two or more compounds, and
the chemical structural formula of said compound or of said two or more compounds, or
a program routine for preparing the chemical structural formula of said compound or of said two or more compounds, b) inputting two or more codes into the computer that have each been applied in a readable or machine-readable form to an article with unequivocal association with a compound or a composition, as a result of which the corresponding chemical structural formula of the compound or of each of the compounds in the composition that the code is allocated to is displayed on the display device, and c) manipulating the chemical structural formulae on the display device to prepare the resultant product of the reaction between the compounds or compositions whose codes have been inputted.

2. A method according to claim 1, wherein the code is applied to a container, label, instruction leaflet or list of contents or a table work.

3. A method according to claim 1, wherein the code is applied in the form of a sequence of digits, a bar code or to a magnetic or optical storage medium.

4. A system for representing chemical structural formulae of compounds and of their reaction product or products having an apparatus for carrying out the method according to claim 1, comprising a computer, a symbol or graphic program for the representation of chemical structural formulae, memory, wherein the memory stores the codes, storage space for chemical structures associated with the codes or for program routines producing the representation of said structures, input device for input of the codes, and codes in unequivocal association with the corresponding chemical compounds or compositions in readable form.

5. A system according to claim 4, wherein a bar code reader, a plain text reader or a magnetic strip reader is provided as the device for inputting the codes.

6. A system according to claim 4, wherein the codes are applied to containers, labels or instruction leaflets or lists of contents for the respective chemical compounds or compositions or are stored and can be looked up in a table work.

* * * * *